United States Patent

Middleton

[11] Patent Number: 6,136,031
[45] Date of Patent: Oct. 24, 2000

[54] ARTIFICIAL INTERVERTEBRAL DISC

[75] Inventor: Lance M. Middleton, Trumbull, Conn.

[73] Assignee: Surgical Dynamics, Inc., Norwalk, Conn.

[21] Appl. No.: 09/098,739

[22] Filed: Jun. 17, 1998

[51] Int. Cl.⁷ ............................................. A61F 2/44
[52] U.S. Cl. ............................................... 623/17
[58] Field of Search ............................... 623/17, 16, 18

[56] References Cited

U.S. PATENT DOCUMENTS

| | | | |
|---|---|---|---|
| 4,349,921 | 9/1982 | Kuntz | 623/17 |
| 4,911,718 | 3/1990 | Lee et al. | |
| 4,932,975 | 6/1990 | Main et al. | |
| 5,192,327 | 3/1993 | Brantigan | 623/17 |
| 5,306,308 | 4/1994 | Gross et al. | 623/17 |
| 5,320,644 | 6/1994 | Baumgartner | 623/17 |
| 5,458,638 | 10/1995 | Kuslich et al. | |
| 5,645,598 | 7/1997 | Bronsnahan et al. | |
| 5,674,294 | 10/1997 | Bainville etal. | |
| 5,702,449 | 12/1997 | McKay. | |
| 5,755,798 | 5/1998 | Papavero et al. | 623/17 |
| 5,824,094 | 10/1998 | Serhan et al. | |
| 5,888,227 | 3/1999 | Cottle | 623/17 |

FOREIGN PATENT DOCUMENTS

| | | | |
|---|---|---|---|
| 2004218 | 12/1993 | Russian Federation | 623/17 |

WO 87/07827  12/1998  WIPO.

*Primary Examiner*—Jeffrey A. Smith
*Assistant Examiner*—Eduardo C. Robert

[57] ABSTRACT

An intervertebral prosthesis dimensioned for insertion within an intervertebral space between adjacent vertebrae to replace at least a portion of an intervertebral disc removed therefrom, includes a disc member having sufficient rigidity to support the adjacent vertebrae in spaced relation. The disc member defines a longitudinal axis and a lateral axis transverse to the longitudinal axis. The disc member includes an exterior wall portion having a first slit with a longitudinal component of direction and a second slit with a lateral component of direction. The first and second slits are dimensioned to extend sufficiently within the exterior wall portion and are arranged relative to the longitudinal axis whereby upon insertion of the disc member within the intervertebral space forces exerted on the disc member are transferred along the exterior wall portion as facilitated by the slit arrangement. Preferably, the first slit extends in a general longitudinal direction and the second slit extends in a general lateral direction. The disc member may include an interior cavity disposed within the exterior wall portion with the first and second slits extending through the exterior wall portion in communication with the interior cavity.

24 Claims, 7 Drawing Sheets

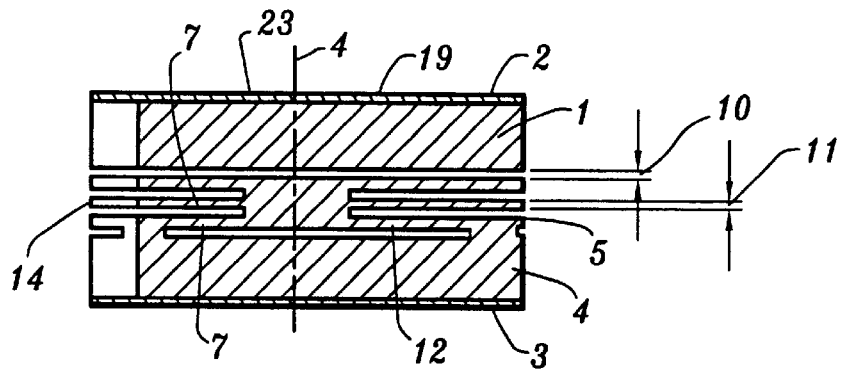
FIG. 2
(PRIOR ART)
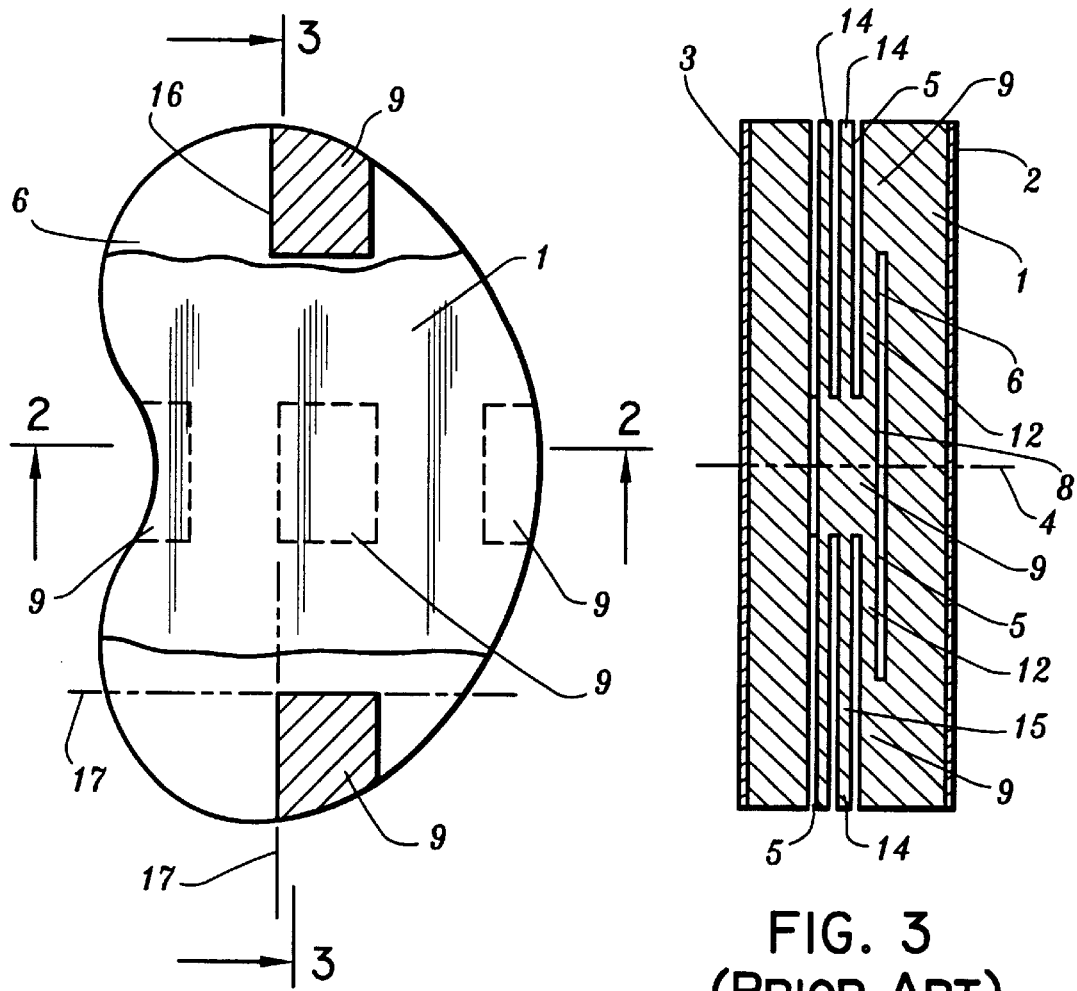
FIG. 3
(PRIOR ART)
FIG. 1
(PRIOR ART)

ARTIFICIAL INTERVERTEBRAL DISC

BACKGROUND

1. Field of the Disclosure

The present disclosure generally relates to apparatus and techniques for treatment of spinal disorders, and, in particular, relates to an artificial intervertebral prosthesis which restores both the height and shape of the intervertebral disc space following the removal of a damaged or diseased intervertebral disc while maintaining the natural biomechanics of the spinal motion segment.

2. Description of the Prior Art

The objective in inverterbral disc replacement is to provide a prosthetic disc that combines both stability to support the high loads of the patient's vertebrae and flexibility to provide the patient with sufficient mobility. In attempting to strike this balance, generally, four basic types of artificial intervertebral discs for replacing a part or all of a removed disc have been developed, namely, elastomer discs, ball and socket discs, mechanical spring discs and hybrid discs. Elastomer discs typically include an elastomer cushion which is sandwiched between lower and upper rigid endplates. The elastomer discs are advantageous in that the elastomer cushion functions similar in mechanical behavior to the removed intervertebral disc tissue. However, a disadvantage of this disc type is that the elastomer cushion experiences long term in-vivo problems stemming from microcracking, which detracts from its usefulness as a replacement option. Furthermore, attachment of the elastomer cushion to the endplates presents additional difficulties. Examples of elastomer discs are disclosed in U.S. Pat. Nos. 5,702,450 to Bisserie; 5,676,792 to Ratron; 5,035,716 to Downey; 4,874,389 to Downey; and 4,863,477 to Monson.

Ball and socket discs typically incorporate two plate members having cooperating inner ball and socket portions which permit articulating motion of the members during movement of the spine. The ball and socket arrangement is adept in restoring "motion" of the spine, but, is poor in replicating the natural stiffness of the intervertebral disc. This low stiffness places detrimentally high loads on supporting ligaments and muscles, particularly, in movement involving torsional rotation of the spine. Dislocation and wear are other concerns with this disc type. Examples of ball and socket discs are disclosed in U.S. Pat. Nos.: 5,507,816 to Bullivant and 5,258,031 to Salib et al.

Mechanical spring discs usually incorporate one or more coiled springs disposed between metal endplates. The coiled springs preferably define a cumulative spring constant sufficient to maintain the spaced arrangement of the adjacent vertebrae and to allow normal movement of the vertebrae during flexion and extension of the spring in any direction. Disadvantages of the mechanical spring disc types involve attachment of the coiled springs to the metal end plates and associated wear at the attachment points. Furthermore, fibrous tissue growth or encroachment into the coiled springs presents additional difficulties. Examples of mechanical spring discs are disclosed in U.S. Pat. Nos. 5,458,642 to Beer et al. and 4,309,777 to Patil.

The fourth type of artificial intervertebral disc, namely, the hybrid type incorporates two or more principles of any of the aforedescribed disc types. For example, one known hybrid disc arrangement includes a ball and socket set surrounded by an elastomer ring. This hybrid disc provides several advantages with respect to load carrying ability, but, is generally complex requiring a number of individual components. Furthermore, long term in vivo difficulties with the elastomer cushion remain a concern as well as wear of the ball and socket arrangement.

Another type of intervertebral disc prosthesis is disclosed in U.S. Pat. No. 5,320,644 to Baumgartner. With reference to FIGS. 1–3, the Baumgartner '644 device is a unitary intervertebral disc member 1 made from a strong, elastically deformable material. The disc member 1 has parallel slits 5 each arranged at a right angle to the axis of the disc member. The parallel slits 5 partially overlap one another to define overlapping regions 6 between adjacent slits. The overlapping regions 6 create a leaf spring effect for the transmission of forces from one vertebral attachment surface to the other. In regions of adjacent slits 5 where they do not overlap the spring action on the leaf springs 7 is interrupted by fixation zones 9 of solid prosthesis material. The forces acting on the intervertebral disc are transmitted from one leaf spring plane to the next leaf spring plane via the fixation zones 9.

However, the load paths are inherently abrupt with highly localized transfer of load through the sparsely placed fixation zones 9. There are even instances where the entire load is carried through a single fixation zone 9 in the center of the disc. The abrupt load paths can lead to high stress regions, which can detract from the appropriate biomechanical performance, i.e., strength, flexibility, and range-of-motion, of the prosthesis.

The need exists for a prosthetic disk which is easy to manufacture and provides the proper balance of flexibility and stability through improved load distribution.

SUMMARY

Accordingly, the present disclosure relates to an intervertebral prothesis dimensioned for insertion within an intervertebral space between adjacent vertebrae to replace at least a portion of an intervertebral disc removed therefrom. The prosthesis includes a disc member defining a longitudinal axis and a lateral axis transverse to the longitudinal axis. The disc member includes an exterior wall portion having a first slit with a longitudinal component of direction and a second slit with a lateral component of direction. The first and second slits are dimensioned to extend sufficiently within the exterior wall portion and are arranged whereby upon insertion of the disc member within the intervertebral space forces exerted on the disc member are transferred through the slit arrangement along the exterior wall portion. Preferably, the first slit extends in a general longitudinal direction and the second slit extends in a general lateral direction. The disc member may include an interior cavity disposed within the exterior wall portion with the first and second slits extending through the exterior wall portion in communication with the interior cavity.

The disc member may include first and second support surfaces disposed at respective longitudinal ends of the disc member and being dimensioned to supportingly engage vertebral portions of respective vertebrae. At least one of the first and second support surfaces has an opening extending therethrough in communication with the interior cavity. A pair of end caps can also be provided.

In a preferred embodiment, the disc member includes a plurality of lateral slits extending in a general lateral direction and a plurality of longitudinal slits extending in a general longitudinal direction whereby at least two of the lateral slits are longitudinally displaced relative to the longitudinal axis and disposed in at least partial overlapping relation. At least one of the longitudinal slits preferably extends between and interconnects the two lateral slits.

Preferably, at least three lateral slits are longitudinally displaced relative to the longitudinal axis and arranged to define overlapping portions.

BRIEF DESCRIPTION OF THE DRAWINGS

Preferred embodiment(s) of the present disclosure are described herein with reference to the drawings wherein:

FIGS. 1–3 illustrate a prior art intervertebral disc prosthesis;

DETAILED DESCRIPTION OF THE PREFERRED EMBODIMENTS

Figure 4:
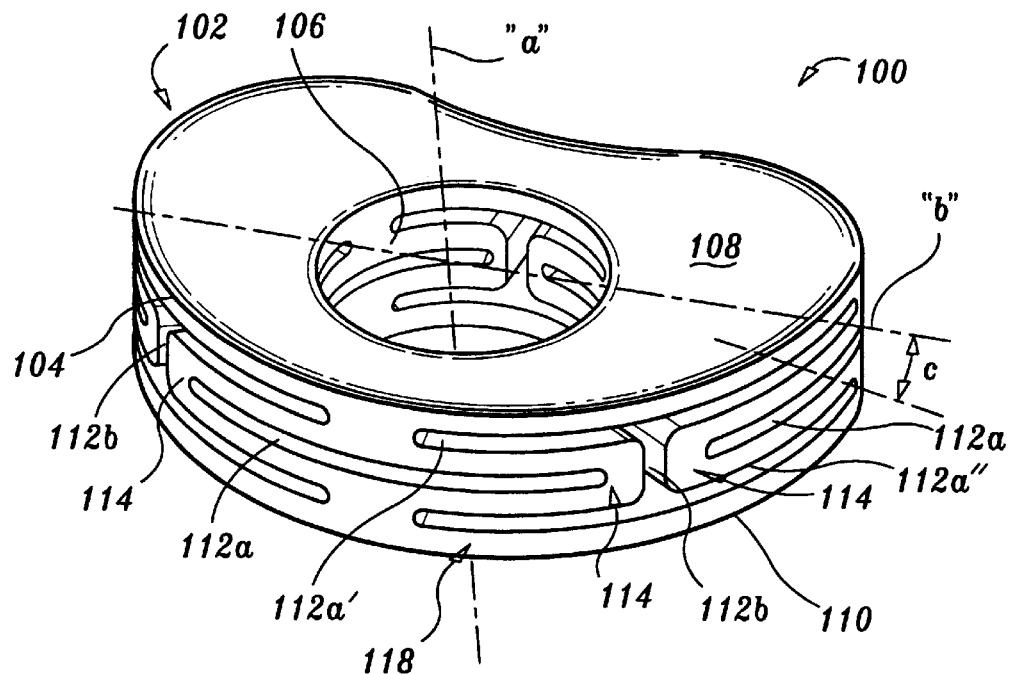
FIG. 4 is a perspective view of the intervertebral disc prosthesis in accordance with the principles of the present disclosure.

Referring now to the drawings, in which like reference numerals identify similar or identical elements throughout the several views, and referring in particular to FIG. 4, the artificial intervertebral prosthesis of the present disclosure is illustrated. Intervertebral prosthesis 100 is intended to replace part or all of the supporting function of a diseased intervertebral disc which had been previously removed through a discectomy procedure or the like. Intervertebral prosthesis 100 is advantageously dimensioned to be positioned between adjacent vertebrae in supporting contacting relation with the vertebral end plates thereof to maintain the adjacent vertebrae in appropriate spaced relation while restoring the natural biomechanics (e.g., including stiffness, range of motion, and load carrying capacity) of the spinal or vertebral segment.

Intervertebral prosthesis 100 includes a single component, namely, disc or body member 102. Body member 102 is in the general shape of an intervertebral disc (e.g., kidney-shaped) as shown and defines longitudinal axis "a" extending the height of the member 102 and radial (lateral) axis "b" generally transverse to the longitudinal axis. An angular reference is defined by "c" as shown in FIG. 4. Body member 102 includes an exterior wall 104 having cannulated bore (interior cavity) 106 defined therein which extends the height of body member 102 in general concentric relation with the longitudinal axis "a". Body member further includes upper and lower longitudinally opposed support surfaces 108, 110 which supportingly engage the respective end faces of the adjacent vertebrae upon insertion of the prosthesis. Support surfaces 108, 110 are each arcuate in configuration defining a slight outer curvature which preferably corresponds to the slight inward curvature of the vertebral end plates so as to facilitate positioning and retention of the prosthesis within the intervertebral space.

With continued reference to FIG. 4, exterior wall 104 includes a plurality of slits 112 defined therein consisting of lateral (radial) slits 112a and longitudinal slits 112b connecting lateral slits 112a. Slits 112a, 112b extend completely through exterior wall 104 from its outer surface to its inner surface in communication with cannulated bore 106. Lateral slits 112a are arranged to be in partial overlapping relation with respect to the longitudinal axis to define overlapping regions 116 within specific radial spaced sections of the body member 102. In the preferred embodiment, the overlapping regions 116 include portions of three lateral slits 112a. The longitudinal slit 112b connect upper slits 112a' and lower slits 112a" at approximately 90° intervals to help transfer the load by providing a continuous load path.

Lateral slits 112a and longitudinal slits 112b are arranged in radial patterns so that their interconnectivity forms flexible load paths 114 between the support surfaces 108, 110. In the preferred embodiment, the longitudinal slits 112b connect upper slits 112a' and lower slits 112a" at approximately 90° intervals resulting in the continuous load path 114 that is piecewise smooth.

It is also envisioned that diagonally oriented (i.e. having a longitudinal and lateral component) slits can be provided to interconnect upper and lower slits 112a' and 112a". Similarly, diagonally oriented slits can be provided to interconnect with longitudinal slits 112b. In each of these alternate embodiments, the disk prosthesis includes a slit arrangement having lateral and longitudinal components. In these arrangements, the interconnection of slits form slits of multi-directional paths that are piecewise smooth. However, it is also envisioned that the multi-directional slits can be curved slits that follow a smooth path.

The pattern of slits 112 provides a spring-like characteristic to the prosthesis 100 whereby the load forces are transferred between upper support surface 108 and lower support surface 110 through continuous load paths 114. This pattern is advantageously dimensioned to reduce the rigidity of the prosthesis to permit flexural movement of the spine while retaining adequate strength to maintain the disc in spaced relation.

The components of intervertebral prosthesis 100 are fabricated from a suitable rigid material including stainless steel, titanium or a suitable polymeric material. Preferably, the body member 102 is monolithically formed from titanium as a single unit although it is envisioned that in an alternate embodiment, the body member 102 is composed of separate components, each of which would have the structural features, multi-directional slits, and inner cavity, discussed above. For example, three components can be utilized which when placed in juxtaposition in the invertebral space form the kidney shape of FIG. 4.

Insertion of the Artificial Intervertebral Disc

Figure 5:
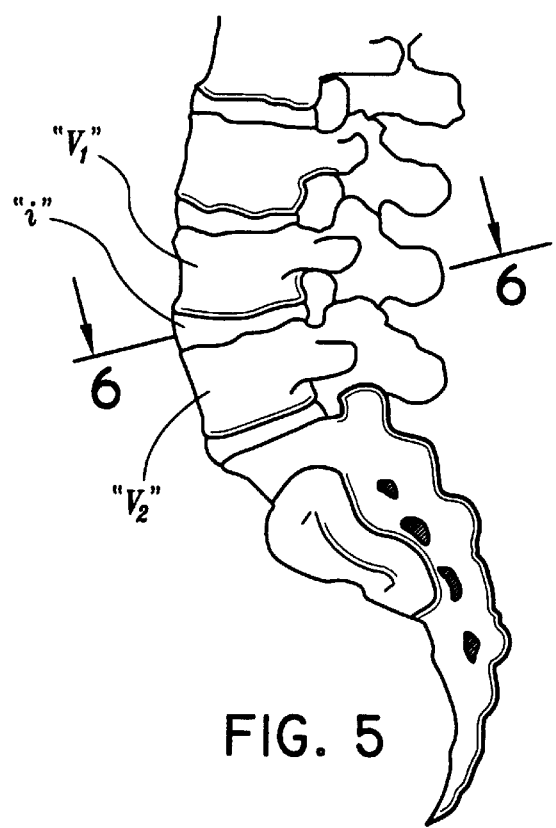
FIG. 5 is a view illustrating a portion of the vertebral column.
Figure 6:
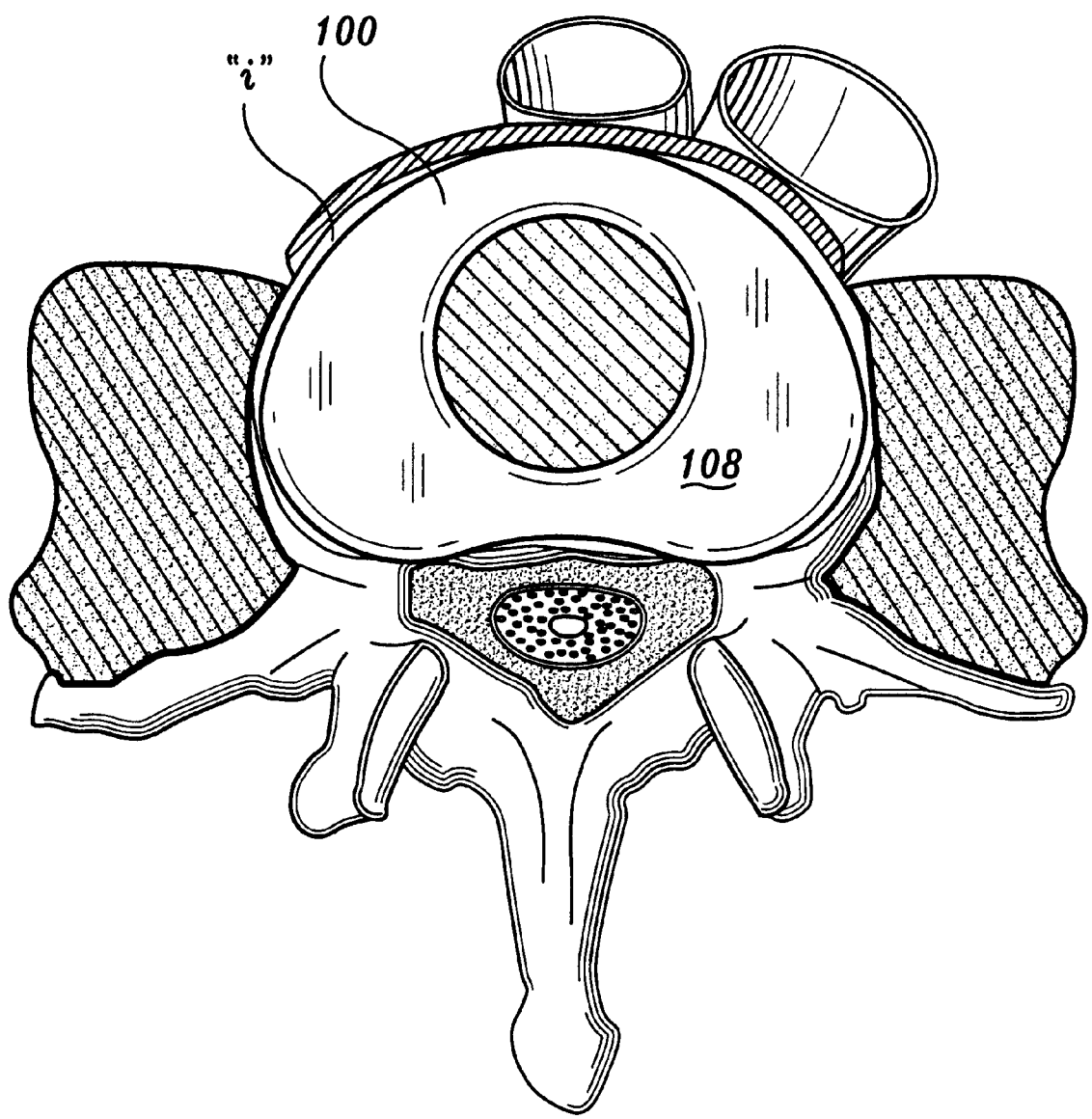
FIG. 6 is a view taken along the lines 6—6 of FIG. 5 illustrating the intervertebral prosthesis of FIG. 4 positioned within the intervertebral space defined between adjacent vertebrae.

With reference to FIGS. 5–6, the insertion of the artificial intervertebral prosthesis will be discussed. The intervertebral space "i" defined between adjacent vertebrae "$V_1$, $V_2$" is accessed utilizing appropriate retractor instrumentation or the like. Thereafter, a partial or full discectomy is performed to remove the diseased portion of the disc. The adjacent vertebrae "$V_1$, $V_2$" are distracted with appropriate distractor instrumentation to expose the intervertebral space. The artificial intervertebral prosthesis 100 is then positioned within the intervertebral space. Upon placement, the upper and lower support surfaces 108, 110 engage the respective vertebral end plates of the adjacent vertebrae "$V_1$, $V_2$" in supporting relation therewith. As noted above, the arcuate contours defined by support surfaces 108, 110 approximates the arcuate contour of the vertebral end plates to snugly fit within the adjacent vertebrae "$V_1$, $V_2$" and facilitate retention within the intervertebral space.

As indicated hereinabove, the artificial intervertebral prosthesis 100 maintains the adjacent vertebrae "$V_1$, $V_2$" in spaced relation. Loads applied to the intervertebral prosthesis 100 are transmitted between the upper and lower support surfaces 108, 110 along exterior wall 104 through the continuous load paths 114. Moreover, the loads are transmitted in a generally continuous manner with no abrupt load stoppages.

Alternate Embodiment(s)

Figure 7:
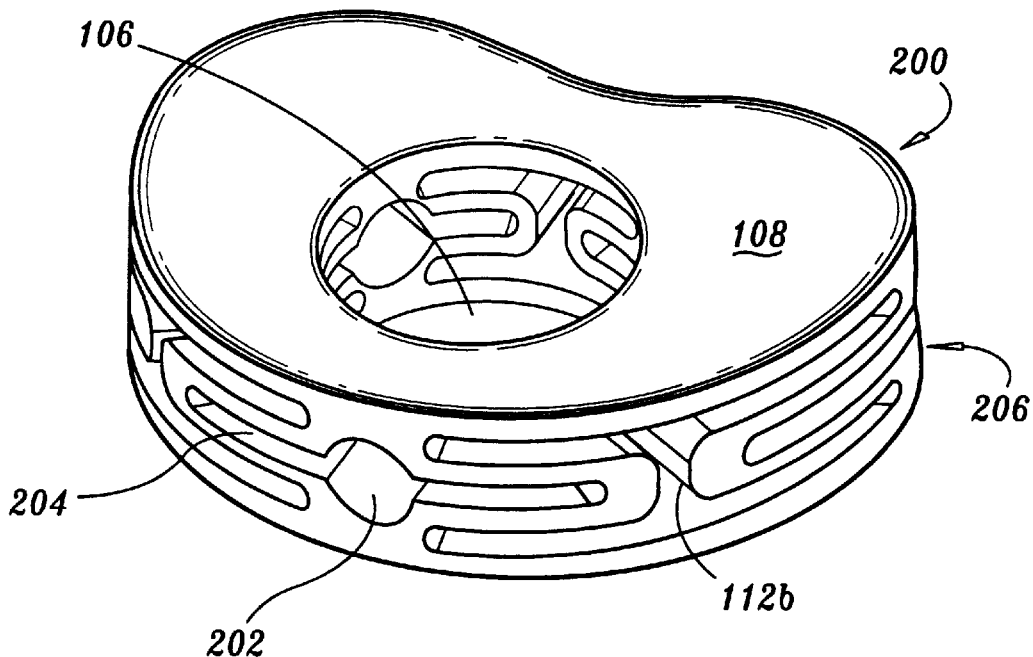
FIG. 7 is a perspective view of an alternate embodiment of the artificial intervertebral disc prosthesis.

FIG. 7 illustrates an alternate embodiment of the present disclosure. Prosthesis 200 is substantially similar to the embodiment of FIG. 4, but, further includes an arcuate cut-out or aperture 202 in communication with each central transverse slit 204, creating a slit with a non-uniform width. Aperture 202 extends completely through exterior wall 206 in communication with cannulated bore 106, and with its larger width is advantageously dimensioned to further reduce the rigidity of the prosthesis 200.

Figure 8:
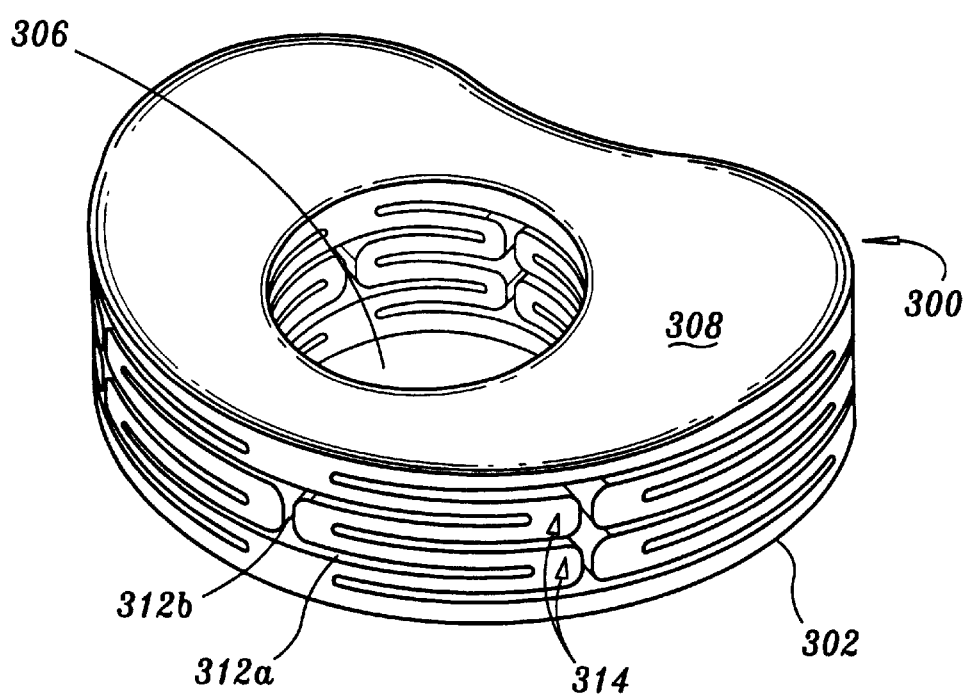
FIG. 8 is a perspective view of another alternate embodiment of the intervertebral disc prosthesis.

FIG. 8 illustrates another alternate embodiment of the present disclosure. Intervertebral prosthesis 300 includes body member 302 with bore 306 and top surface 308 which is substantially similar to body member 102 of the embodiment of FIG. 4. However, in accordance with this embodiment, an additional series of longitudinal and lateral slits 312a, 312b are provided to define at least two additional levels of slits to increase the flexibility of the prosthesis 300. The load paths are designated by reference numeral 314.

Figure 9:
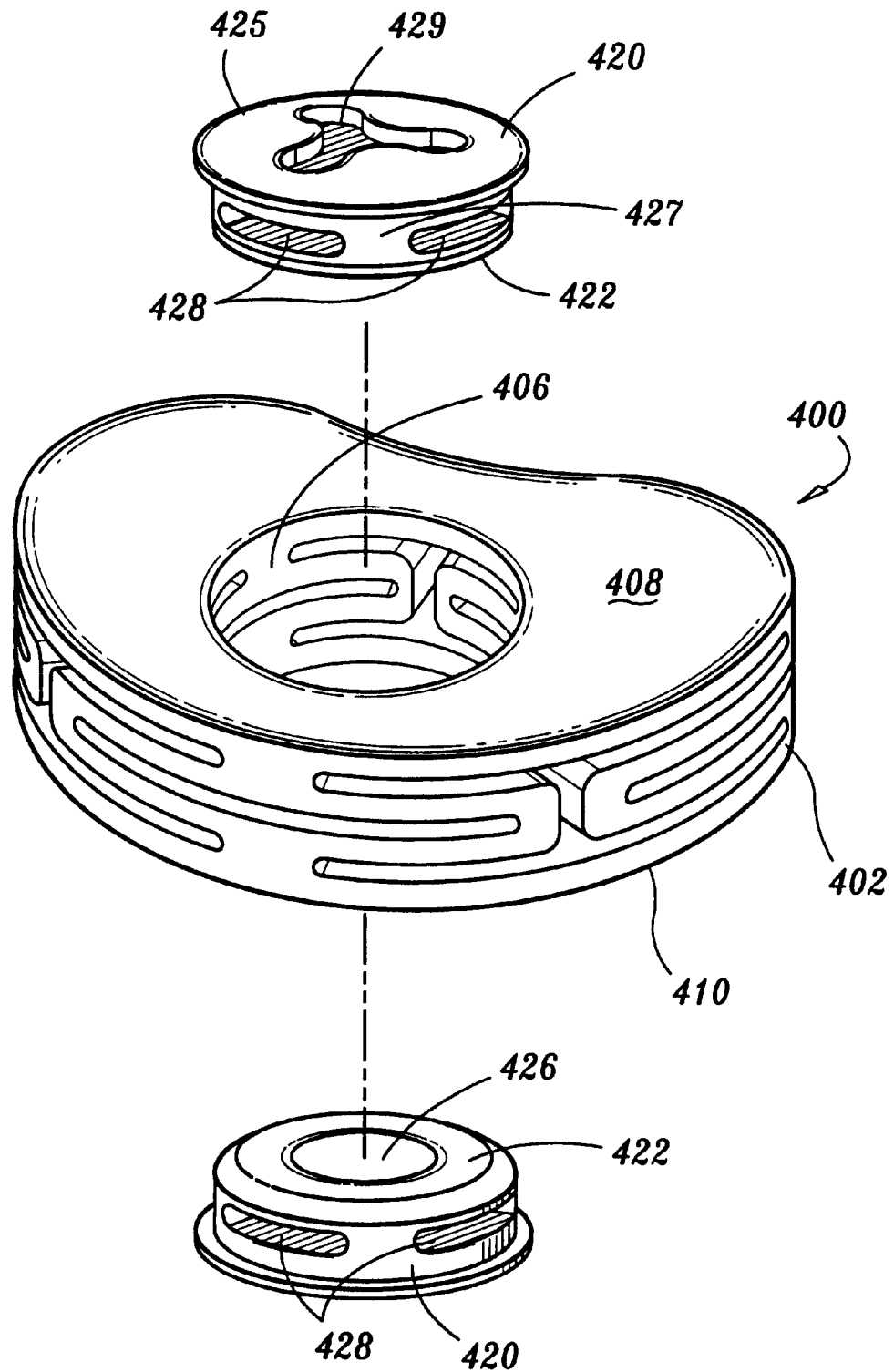
FIG. 9 is a perspective view of an alternate embodiment of the invertebral disc prosthesis having a pair of end caps.

FIG. 9 illustrates an alternate embodiment 400 of the present disclosure having end caps 420. End caps 420 can be placed in central bore 406 of body member 402 as in FIG. 9 to be flush with upper and lower surfaces 408, 410 or alternatively surfaces 408, 410 can be formed without an opening to provide a solid surface 408, 410 on the upper and lower sides of bore 406.

End caps 420 are at least partially received within central bore 406 in a manner whereby circumferential head portion 425 resides in correspondingly dimensioned circumferential recess of the support surface 408, 410 and main portion 427 extends within the bore 406. The outer surface of each end cap 420 is preferably arcuate in shape generally corresponding to the arcuate configuration of the outer support surface 408, 410 to form a smooth transition from the outer support surfaces 408, 410 to the end cap. End caps 420 each further include an indentation 429 defined in portion 425 for attaching an instrument to releasably hold the end cap 420 during insertion into the body member's central bore 406. Indentation 429 is generally clover-shaped although other shapes are contemplated including rectangular, hexagonal, etc. to receive appropriate instrumentation.

The end caps provide additional surfaces for bone attachment and prevent bone growth into the body member. The engagement of the end cap surfaces 422 during high load can serve several purposes: (1) prevents the exterior wall from being overstressed by providing an alternate load path, (2) increases the overall stiffness of the disc (similarly, the natural disc becomes more rigid with high loads), (3) prevents complete closure of the multi-directional slits, relieving a "pinching" effect on surrounding soft tissue. Internal bore 426 with its associate slotted openings 428 effectively reduce the rigidity of the end caps so that the overall stiffness of the disc prosthesis will be more consistent with the natural intervertebral disc.

Fusion Cage with Slit(s)

Figure 10A:
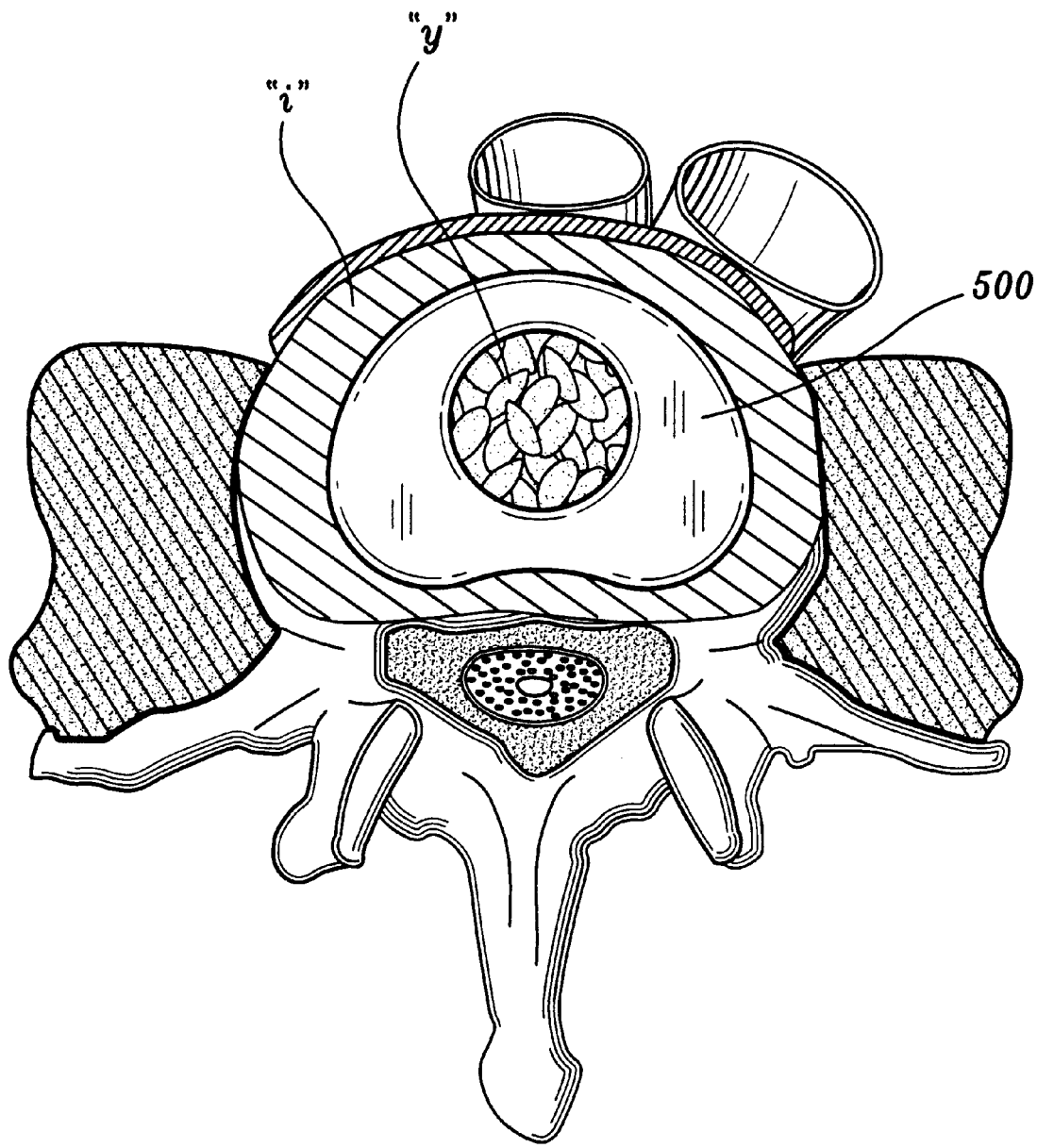
FIG. 10A is a cross-sectional view taken through the vertebral body to illustrate a top view of the fusion cage of the present disclosure.
Figure 10B:
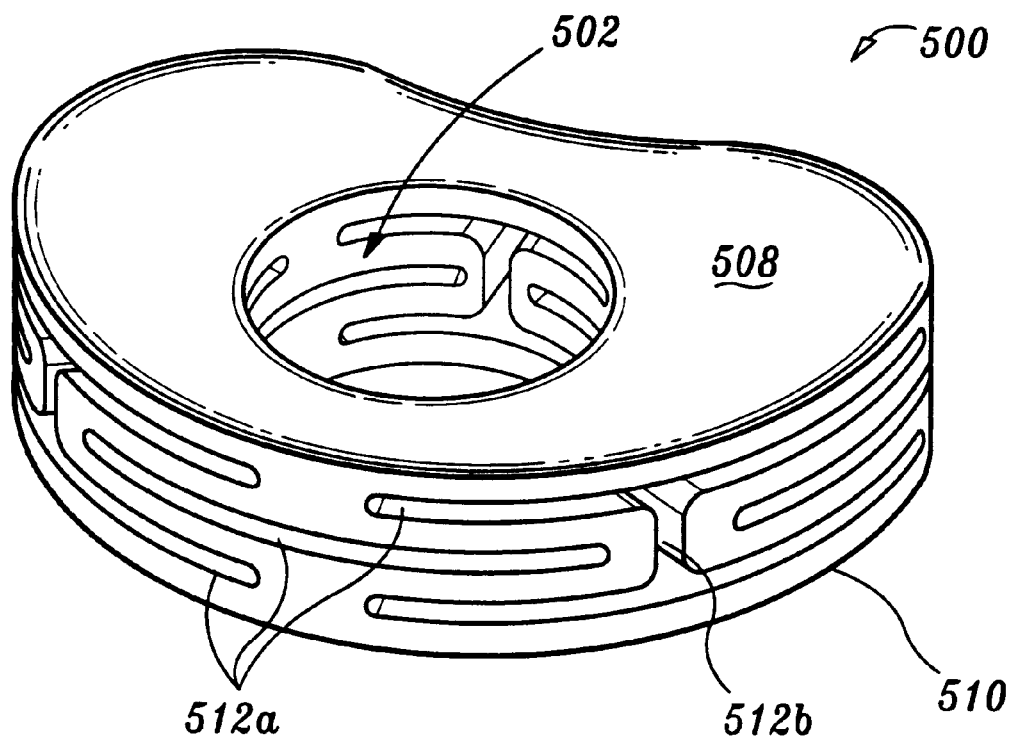
FIG. 10B is a perspective view of the fusion cage of FIG. 10A.

The present disclosure also includes a unique fusion cage illustrated in FIGS. 10A and 10B and designated generally reference numeral 500. In the use of spinal fusion cages, load sharing with the bone graft packed within the cage is necessary to transform the bone graft in to a solid bony arthrodesis. With current fusion cages, such as these made of titanium alloy, the cage is rigid, resulting in the cage as the dominant load path during the fusion process.

The fusion cage 500 of the present disclosure is preferably composed of a titanium alloy. However, the cage includes a slit configuration to reduce stiffness. That is, the lateral and longitudinal slits 512a and 512b provide the cage with additional flexibility so it flexes under load, resulting in greater load sharing with the graft. As can be appreciated, fusion cage 500 has the identical slit configuration as the prosthetic disc of FIG. 4, and therefore the slit configuration will not be described again. Note that the slit design of FIGS. 7 and 8 can also be utilized.

Cage 500 includes an internal cavity or bore 502 to receive bone graft material "g" (see FIG. 10A and 11A). End caps (not shown) of the type illustrated in FIG. 9 can be provided to help retain the bone graft material and to limit flexure as described above, as long as the caps have openings communicating with the internal cavity 502 to ensure contact between the bone graft material "g" and vertebrae. Once the cage 500 is placed in the vertebral space "i" with support surfaces 508, 510 contacting the vertebrae, this bone graft material inside cavity 502 fuses with the adjacent vertebrae over time. As shown in FIG. 10A, as with current fusion cages, cage 500 is smaller than the overall disc space. Although one is shown, it is contemplated that two or more cages 500 can be placed side by side in the disc space.

Also, since fusion cage 500 does not fill the entire disc space, shapes other than the kidney shape of FIG. 10A and 10B are also contemplated, provided they contain the slit configuration to reduce overall flexibility.

It will be understood that various modifications may be made to the embodiment disclosed herein. Therefore, the above description should not be construed as limiting but merely as an exemplification of a preferred embodiment. Those skilled in the art will envision other modifications within the scope and spirit of the claims appended hereto.

What is claimed is:

1. An intervertebral prosthesis, comprising a disc member dimensioned for insertion within an intervertebral space between adjacent vertebrae to replace at least a portion of an intervertebral disc removed therefrom, the disc member defining a longitudinal axis and a lateral axis transverse to the longitudinal axis, the disc member including an exterior wall defining an interior cavity therein, the exterior wall having a first slit with a longitudinal component of direction and a plurality of second slits each with a lateral component of direction, the second slits being arranged in spaced relation along the longitudinal axis and extending to communicate with the interior cavity, the first and second slits dimensioned within the exterior wall portion and being arranged whereby upon insertion of the disc member within the intervertebral space forces exerted on the disc member are transferred along the exterior wall portion.

2. The intervertebral prosthesis according to claim 1 wherein the first slit extends in a general longitudinal direction.

3. The intervertebral prosthesis according to claim 2 wherein the second slits each extend in a general lateral direction.

4. The intervertebral prosthesis according to claim 3 wherein at least two of the second slits are disposed in at least partial overlapping relation with respect to the longitudinal axis.

5. The intervertebral prosthesis according to claim 4 wherein at least five of the second slits are disposed in at least partial overlapping relation with respect to the longitudinal axis.

6. The intervertebral prosthesis according to claim 3 wherein the first slit extends through the exterior wall and communicates with the interior cavity.

7. The intervertebral prosthesis according to claim 6 wherein the disc member includes first and second support surfaces disposed at respective longitudinal ends of the disc member and being dimensioned to supportingly engage vertebral portions of respective vertebrae.

8. The intervertebral prosthesis according to claim 7 wherein the disc member is monolithically formed having the first and second support surfaces formed therewith.

9. The intervertebral prosthesis according to claim 7 wherein at least one of the first and second support surfaces has an opening extending therethrough in communication with the interior cavity.

10. The intervertebral prosthesis according to claim 9 including an end cap mountable to the one support surface and at least partially positionable within the opening.

11. The intervertebral prosthesis according to claim 9 wherein each of the first and second support surfaces has an opening extending therethrough in communication with the interior cavity.

12. An intervertebral prosthesis, which comprises a disc member dimensioned for insertion within an intervertebral space between adjacent vertebrae to replace at least a portion of an intervertebral disc removed therefrom, the disc member defining a longitudinal axis and a lateral axis transverse to the longitudinal axis, the disc member including an exterior wall defining an interior cavity, the exterior wall having a plurality of lateral slits extending in a general lateral direction and at least one longitudinal slit extending in a general at least one of the plurality of lateral slits longitudinal direction and communicating with the interior cavity, the one longitudinal slit dimensioned to extend and interconnect two longitudinally spaced lateral slits.

13. The intervertebral prosthesis according to claim 12 including at least three lateral slits longitudinally displaced relative to the longitudinal axis and arranged to at least partially overlap to define overlapping portions.

14. The intervertebral prosthesis according to claim 12 wherein at least two of the lateral slits are longitudinally displaced relative to the longitudinal axis and disposed in at least partial overlapping relation, the one longitudinal slit extending between the at least two lateral slits.

15. The intervertebral prosthesis according to claim 14 further comprising a plurality of spaced apart longitudinal slits, each longitudinal slit interconnecting respective two longitudinally spaced lateral slits.

16. The intervertebral prosthesis according to claim 15 wherein the lateral slits each extend through the exterior wall in communication with the interior cavity.

17. An intervertebral prosthesis, comprising a body member dimensioned for insertion within an intervertebral space between adjacent vertebrae to replace at least a portion of an intervertebral disc removed therefrom, the body member having an outer wall defining an internal cavity, a longitudinal axis and a lateral axis transverse to the longitudinal axis, the outer wall having first, second and third slits defined therein, the first and second slits having a lateral component of direction and the third slit having a longitudinal component of direction and interconnecting the first and second slits, at least one of the first, second and third slits extending through the outer wall in communication with the internal cavity.

18. The intervertebral prosthesis according to claim 17, wherein the first and second slits extend in a general lateral direction.

19. The intervertebral prosthesis according to claim 17, wherein the third slit extends in a general longitudinal direction.

20. The intervertebral prosthesis according to claim 17 wherein each of the first, second and third slits extends through the outer wall in communication with the internal cavity.

21. An intervertebral prosthesis, comprising a body member dimensioned and configured to substantially conform to a general shape of the intervertebral space defined between upper and lower adjacent vertebrae to supportingly engage an adjacent vertebrae to maintain the adjacent vertebrae in spaced relation, the body member defining a longitudinal axis and a lateral axis transverse to the longitudinal axis, the body member including upper and lower support surfaces disposed at respective longitudinal ends of the body member and being dimensioned to supportingly engage respective upper and lower vertebral portions of the adjacent vertebrae, the body member having a central longitudinal opening extending through the upper and lower support surfaces, the body member having a plurality of lateral slits extending in a general lateral direction and at least one longitudinal slit extending in a general longitudinal direction, at least two of the lateral slits longitudinally and radially displaced relative to each other.

22. The intervertebral prosthesis according to claim 21 wherein the lateral slits include an upper lateral slit, an intermediate lateral slit longitudinally displaced from the upper lateral slit and a lower lateral slit longitudinally displaced from the upper and intermediate lateral slits, the intermediate slit being radially displaced relative to the upper and lower slits.

23. The intervertebral prosthesis according to claim 22 wherein the at least one longitudinal slit interconnects and communicates with the upper and lower lateral slits without communicating with the intermediate lateral slit.

24. The intervertebral prosthesis according to claim 23 wherein the body member includes an inner cavity, the lateral slits and the one longitudinal slit being dimensioned to communicate with the inner cavity.

* * * * *